US009271905B2

(12) United States Patent
Struillou et al.

(10) Patent No.: US 9,271,905 B2
(45) Date of Patent: Mar. 1, 2016

(54) PROCESS FOR PREPARING POLYUREA MICROCAPSULES

(75) Inventors: Arnaud Struillou, Geneva (CH); Nicolas Pichon, Geneva (CH); Sonia Godefroy, Geneva (CH); Claudie Bellouard Drevet, Geneva (CH)

(73) Assignee: Firmenich S.A., Geneva (CH)

( * ) Notice: Subject to any disclaimer, the term of this patent is extended or adjusted under 35 U.S.C. 154(b) by 181 days.

(21) Appl. No.: 13/700,526

(22) PCT Filed: Jun. 7, 2011

(86) PCT No.: PCT/IB2011/052471
§ 371 (c)(1),
(2), (4) Date: Apr. 24, 2013

(87) PCT Pub. No.: WO2011/154893
PCT Pub. Date: Dec. 15, 2011

(65) Prior Publication Data
US 2013/0230574 A1     Sep. 5, 2013

Related U.S. Application Data

(60) Provisional application No. 61/353,787, filed on Jun. 11, 2010.

(30) Foreign Application Priority Data

Jun. 11, 2010 (EP) ..................................... 10165700
May 18, 2011 (EP) ..................................... 11166533
May 19, 2011 (EP) ..................................... 11166717

(51) Int. Cl.
| | | |
|---|---|---|
| C11D 3/50 | (2006.01) | |
| A61Q 13/00 | (2006.01) | |
| A61K 8/11 | (2006.01) | |
| B01J 13/16 | (2006.01) | |
| C11D 3/37 | (2006.01) | |
| C11D 17/00 | (2006.01) | |
| A61K 8/84 | (2006.01) | |
| A61Q 5/02 | (2006.01) | |
| A61Q 5/12 | (2006.01) | |
| A61Q 19/10 | (2006.01) | |

(52) U.S. Cl.
CPC ... *A61K 8/11* (2013.01); *A61K 8/84* (2013.01); *A61Q 13/00* (2013.01); *B01J 13/16* (2013.01); *C11D 3/3726* (2013.01); *C11D 3/505* (2013.01); *C11D 17/0039* (2013.01); *A61Q 5/02* (2013.01); *A61Q 5/12* (2013.01); *A61Q 19/10* (2013.01)

(58) Field of Classification Search
CPC ...... A61K 8/11; C11D 3/505; C11D 17/0039; C11D 3/3726; A61Q 13/00; A61Q 5/12; A61Q 19/10; A61Q 5/02; B01J 13/16
See application file for complete search history.

(56) References Cited

U.S. PATENT DOCUMENTS

| | | | |
|---|---|---|---|
| 3,886,085 A | 5/1975 | Kiritani et al. | ................. 252/316 |
| 4,668,580 A | 5/1987 | Dahm et al. | ............. 428/402.21 |
| 4,847,152 A * | 7/1989 | Jabs et al. | ................. 428/402.21 |
| 2007/0042182 A1 * | 2/2007 | Markus et al. | ............. 428/402.2 |
| 2007/0202063 A1 | 8/2007 | Dihora et al. | ................. 424/70.1 |
| 2007/0220686 A1 | 9/2007 | Jeanne-Rose et al. | ............ 8/406 |

FOREIGN PATENT DOCUMENTS

| | | |
|---|---|---|
| EP | 1 741 775 A1 | 1/2007 |
| GB | 2 432 843 A | 6/2007 |
| GB | 2 432 850 A | 6/2007 |
| GB | 2 432 851 A | 6/2007 |
| GB | 2 432 852 A | 6/2007 |
| WO | WO 2004/098767 A1 | 11/2004 |
| WO | WO 2005/054422 A1 | 6/2005 |
| WO | WO 2007/062733 A1 | 6/2007 |
| WO | WO 2007/062833 A1 | 6/2007 |
| WO | WO 2008/016684 A1 | 2/2008 |
| WO | WO 2009/091726 A1 | 7/2009 |

OTHER PUBLICATIONS

International Search Report and Written Opinion of the International Searching Authority, application No. PCT/IB2011/052471, mailed Sep. 7, 2011.

* cited by examiner

*Primary Examiner* — Abigail Fisher
*Assistant Examiner* — Daniel L Branson
(74) *Attorney, Agent, or Firm* — Winston & Strawn LLP

(57) ABSTRACT

The present invention relates to a process for producing perfume-containing microcapsules with a polyurea wall that can be used in home or personal care products, as well as to the microcapsules themselves and consumer products that contain these microcapsules. The process of the invention uses a combination of aromatic and aliphatic polyisocyanates in specific relative concentrations.

20 Claims, 2 Drawing Sheets

PROCESS FOR PREPARING POLYUREA MICROCAPSULES

TECHNICAL FIELD

The present invention relates to a process for producing perfume-containing microcapsules with a polyurea wall that can be used in home or personal care products, as well as to the microcapsules themselves and consumer products comprising these microcapsules.

The process of the invention uses a combination of aromatic and aliphatic polyisocyanates in specific relative concentrations.

BACKGROUND OF THE INVENTION AND PROBLEM TO BE SOLVED

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner.

Polyurea capsules, formed by polymerisation between a polyisocyanate and a polyamine, are well known capsules that are used in a large variety of technical fields, including perfumery. However, such delivery systems may suffer from stability problems when incorporated into surfactant based products such as detergents or fabric-softeners, which are strongly aggressive towards said delivery systems.

It is especially difficult to prepare capsules having both good stability and good olfactive performance. The perfume retention ability, and therefore the ability of the capsules to avoid loss of the volatile ingredients, is in particular dependent on the stability of the capsules in the product base. On the other hand, the hedonic effect perceived by the consumer using a perfumed product, and therefore its perception of the quality of such a product, depends on the olfactive performance of the capsules. In particular, capsules having a good stability in a product base do not automatically have good olfactive performance. It is therefore desirable to provide capsules having both good stability and good olfactive performance.

Several prior art documents address the problem of the stability of polyurea microcapsules.

This is for example the case of U.S. Pat. No. 3,886,085, which discloses a process for the preparation of microcapsules of fine oil droplets employing a polyisocyanate adduct having a free isocyanate group and a polyamine or a polyamine adduct having a free amino group. Among the polyisocyanate adducts that can be used, aromatic ones are mentioned. Such a process allegedly produces capsules encapsulating a perfume, wherein the perfume can be preserved for a long period of time without being released through the capsule walls or shells (i.e. stable capsules). However, the capsules are specifically designed to be applied on paper. It is well known that the presence of surfactants in perfumed products such as home- and personal-care products renders these product bases very aggressive to capsules incorporated therein, thus having a very negative impact on the storage stability of the capsules. Such aggressive conditions do not exist when the capsules are applied on paper, so that stability of capsules applied on paper cannot be compared to stability of microcapsules in surfactant-containing mediums, such as perfumed products. Moreover, the problem of the capsules olfactive performance is not addressed in this document.

U.S. Pat. No. 4,668,580 describes a process for the production of polyurea microcapsules, in which a large variety of polyisocyanates can be used including aliphatic and aromatic ones. Example 3 of this document uses a mixture of polyisocyanate consisting of 90% biuretized hexamethylene-diisocyanate and 10% carbodiimide-modified polymethylenepolyphenyldiisocyanate. This document addresses the problem of providing capsules having an "inhomogeneous" organic phase having an organic liquid and a polyisocyanate insoluble therein. The application of this technology in the field of perfumery is not envisaged or even suggested in this document. Therefore, the problem of combining both storage stability of perfume capsules and good olfactive performance is not addressed in this document.

The present invention provides a new process for the preparation of polyurea microcapsules. It advantageously solves the problem of providing highly stable capsules having at the same time good olfactive performance. The present solution to this problem is not described or even suggested in any prior art document.

SUMMARY OF THE INVENTION

The present invention relates to a process for preparing polyurea microcapsules encapsulating a perfume. The invention concerns the capsules themselves as well as perfuming compositions and perfumed articles containing them.

DETAILED DESCRIPTION OF THE INVENTION

One object of the present invention is a process for the preparation of polyurea microcapsules comprising
   a) dissolving a mixture of at least one aliphatic polyisocyanate and of at least one aromatic polyisocyanate, both comprising at least two isocyanate functional groups, in a perfume to form a solution;
   b) adding to the mixture obtained in step a) an aqueous solution of an emulsifier or of a colloidal stabilizer;
   c) adding to the mixture obtained in step b) a polyamine to form a polyurea wall with the polyisocyanate, so as to form a microcapsules slurry;
characterized in that the aliphatic polyisocyanate and the aromatic polyisocyanate are used in a respective molar ratio ranging from 80:20 to 10:90.

The perfume in which the polyisocyanate is dissolved in step a) can be a perfuming ingredient alone or a mixture of ingredients in the form of a perfuming composition. Any perfuming ingredient or composition can be used. Specific examples of such perfuming ingredients may be found in the current literature, for example in Perfume and Flavour Chemicals, 1969 (and later editions), by S. Arctander, Montclair N.J. (USA), as well as in the vast patent and other literature related to the perfume industry. They are well known to the person skilled in the art of perfuming consumer products, that is, of imparting a pleasant odor to a consumer product.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn®. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

According to a preferred embodiment of the invention, the perfume used in the process of the invention contains less than 10% of its own weight of primary alcohols, less than 15% of its own weight of secondary alcohols and less than 20% of its own weight of tertiary alcohols. Preferably, the perfume used in the process of the invention does not contain any primary alcohols and contains less than 15% of secondary and tertiary alcohols.

According to another preferred embodiment of the invention, there is used an amount of between 25 and 60% of perfume in the process of the invention, these percentages being defined by weight relative to the total weight of the obtained microcapsules slurry.

The polyisocyanates used in the process of the invention comprise at least two isocyanate groups. Preferably they contain at least three isocyanate groups. Following these numbers of functional groups, an optimal reticulation or network of the capsules wall is achieved, providing thus microcapsules exhibiting a prolonged slow release of fragrances, as well as a good stability in the consumer product.

Low volatility polyisocyanates are preferred because of their low toxicity.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets and polyisocyanurates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). The chemical structures of these preferred aromatic polyisocyanates are represented in FIG. 1. In a most preferred embodiment, the aromatic polyisocyanate is a trimethylol propane-adduct of xylylene diisocyanate.

The term "aliphatic polyisocyanate" is defined as a polyisocyanate which does not comprise any aromatic moiety. Preferred aliphatic polyisocyanates are a trimer of hexamethylene diisocyanate, a trimer of isophoronc diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred. The chemical structure of this preferred aliphatic polyisocyanate is represented in FIG. 1.

Examples of preferred specific mixtures of at least one aliphatic polyisocyanate and of at least one aromatic polyisocyanate are a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate.

In a preferred embodiment, the at least one aliphatic polyisocyanate and the at least one aromatic polyisocyanate are used in a respective molar ratio comprised between 75:25 and 20:80, more preferably between 60:40 and 20:80, even more preferably between 60:40 and 30:70, most preferably between 45:55 and 30:70.

Preferably the polyisocyanate mixture is added in an amount comprised between 2 and 20% by weight, relative to the total weight of the solution obtained in step a).

In step b) of the process of the present invention an aqueous solution of an emulsifier or of a colloidal stabilizer is added to the mixture of step a). In a preferred embodiment, a dispersion or an emulsion is formed wherein droplets of the mixture obtained in step a) are dispersed throughout the aqueous solution of the emulsifier or colloidal stabilizer. For the purpose of the present invention, an emulsion is characterized by the stabilization of the oil droplets by emulsifiers, while in a dispersion the droplets are stabilized by a colloidal stabilizer. The dispersion or emulsion may be prepared by high shear mixing and adjusted to the desired droplet size. Droplet size may be checked with light scattering measurements or microscopy. Preferably an aqueous solution of a colloidal stabilizer is used and therefore a dispersion is formed.

Examples of colloidal stabilizers are polyvinyl alcohol, cellulose derivatives such as hydroxyethyl cellulose, polyethylene oxide, copolymers of polyethylene oxide and polyethylene or polypropylene oxide, copolymers of acrylamide and acrylic acid or cationic polymers such as for example a cationic copolymer of vinylpyrrolidone and of a quaternized vinylimidazol such as those sold under the trade name Luviquat® (commercially available from BASF). Preferably, the colloidal stabilizer is polyvinyl alcohol or a cationic polymer, which is a copolymer of vinylpyrrolidone and of a quaternized vinylimidazol, or a mixture thereof.

Examples of emulsifiers are anionic surfactant such as sodium dodecyl sulfate or Stepantex® (commercially available from Stepan), non ionic surfactant such as diblock copolymers of polyethylene oxide and polyethylene or polypropylene oxide.

In step c) of the process of the invention, a polyamine is added. The polyurea wall of the microcapsules is the result of the interfacial polymerisation between the polyisocyanate dissolved in step a) and the polyamine added in step c).

For the purpose of the present invention, the polyamine may be used alone, or be admixed with glycerine.

Preferably said polyamine is selected from the group consisting of 1,2-diaminopropane, 1,2-diaminoethane, diethylenetriamine, water soluble guanidine salts and guanidine, tris-(2-aminoethyl)amine, N,N'-bis(3-aminopropyl)-ethylenediamine and N,N,N',N'-tetrakis(3-aminopropyl)-1,4-butanediamine. The chemical structures of these preferred polyamines are represented in FIG. 1.

More preferably, the polyamine is selected from the group consisting of water-soluble guanidine salts and guanidine, tris-(2-aminoethyl)amine, N,N'-bis(3-aminopropyl)-ethylenediamine and N,N,N',N'-tetrakis(3-aminopropyl)-1,4-butanediamine. Most preferably it is selected from guanidine, water-soluble guanidine salts and N,N'-bis(3-aminopropyl)-ethylenediamine. By "water soluble guanidine salt" it is meant a salt soluble in water and resulting from the reaction of guanidine with an acid. One example of such salts is guanidine carbonate.

The amount of polyamine used is typically adjusted so that, for each mole of isocyanate group dissolved in the perfume of step a), there is added from 0.5 to 3 moles of amine groups in step c). Preferably, for each mole of isocyanate group dissolved in the perfume in step a), 1 to 3, more preferably 1 to 2 moles of amine groups are added in step c).

No specific action is required to induce the polymerisation between the polyisocyanates and the polyamine. The reaction starts immediately after adding the polyamine. Preferably the reaction is maintained for 2 to 15 hours, more preferably for 2 to 10 hours.

The specific composition of the polyurea wall is key in obtaining microcapsules that are at the fine balance between release and retention so as to achieve satisfactory release of fragrances, once the capsules are placed on textiles or hair, while showing the desired stability in the product base (e.g. counteracts efficiently the extraction of the perfume by the surfactants of the consumer product). Therefore the selection of the polyamine and of the polyisocyanate, among the ones mentioned above, enables the fine tuning of the properties and stability of the capsules.

In an optional step of the process of the invention, the microcapsules can be isolated from the slurry. In another optional step, the microcapsules slurry can be dried in a generally known manner to form a polyurea microcapsules powder. Any drying method known to a person skilled in the art can be used and in particular the slurry may be spray dried to provide a microcapsule powder.

The microcapsules obtained by the process of any of the above-described embodiments are also an object of the present invention. Therefore the present invention provides microcapsules comprising
a polyurea wall, which comprises the reaction product of the polymerisation between at least one polyisocyanate and at least one polyamine;
a colloidal stabilizer or an emulsifier; and
an encapsulated perfume;
characterized in that the polyisocyanate is in the form of a mixture of at least one aliphatic polyisocyanate and at least one aromatic polyisocyanate in a respective molar ratio comprised between 80:20 to 10:90, both the aromatic and the aliphatic polyisocyanate comprising at least two isocyanate functional groups.

According to a preferred embodiment, the polyurea wall is the reaction product of the polymerisation between at least one polyisocyanate and at least one polyamine.

The microcapsules obtained have an average diameter (d(v, 0.5)) comprised between 1 and 50 µm and preferably comprised between 5 and 35 µm, more preferably between 5 and 20 µm. In the present context, "average diameter" refers to the arithmetic mean. The present inventors have found that with microcapsules of this size, optimal deposition and/or adherence of microcapsules to the targeted surface, e.g. textile, hair or skin, is obtained.

The polyisocyanate mixture, the perfume, the colloidal stabilizer or emulsifier and the polyamine, as well as the respective amounts of these components, are as defined above in any embodiment related to the process of preparation of the microcapsules.

The microcapsules of the invention can be advantageously used for the controlled release of the encapsulated perfume. It is therefore particularly appreciated to include these microcapsules as perfuming ingredients in a perfumed consumer product. This result is highly surprising since said consumer products may contain high amounts (typically more than 10% of their own weight) of specific types of surfactant/tensioactive/solvents and which are known to significantly diminish the stability and the performance of said capsules. In other words, the use of the invention's microcapsules in the consumer products provides unexpected advantages over the same use of other similar prior art capsules.

As shown in the examples below, the polyurea microcapsules obtained by the process of the invention provide a good retention of the perfume, while having good olfactive performance. They provide a controlled release of the encapsulated perfume, said perfume being slowly released from the microcapsules, thus considerably improving the perfume long-lastingness and intensity.

The capsules of the present invention have the advantage of being stable. More preferably, the microcapsules are considered as stable when not more than 50% of the initial perfume load leaks out of the capsules when they are stored for one month at 38° C. when they are incorporated in a consumer product, for example one of the consumer products listed below.

A perfumed consumer product comprising the microcapsules of the invention is therefore also an object of the present invention. In particular the consumer product may be in the form of a home- or personal-care product or in the form of a fine fragrance product. Examples of personal-care products include shampoos, hair conditioners, soaps, body washes such as shower or bath salts, mousses, oils or gels, hygiene products, cosmetic preparations, body lotions, deodorants and antiperspirants. Examples of fine fragrance products include perfumes, after-shave lotions and colognes. Examples of home-care products include solid or liquid detergents, all-purpose cleaners, fabric softeners and refreshers, ironing waters and detergents, softener and drier sheets, among which liquid, powder and tablet detergents and fabric softeners are preferred. As detergents we include here products such as detergent compositions or cleaning products for washing up or for cleaning various surfaces, for example intended for the treatment of textiles or hard surfaces (floors, tiles, stone-floors, etc). Preferably the surface is a textile.

Most preferred consumer products include powder and liquid detergents, fabric softeners, body wash, deodorants and antiperspirants, most preferably roll-on deodorants and antiperspirants, hair shampoo, hair conditioners and body lotions.

The capsules slurry obtained in the process of the invention may be used as such to perfume the consumer products. For example, the reaction mixture may be directly added to a liquid fabric softener. Alternatively, the microcapsules obtained in the process of the invention may be isolated from the reaction mixture before being incorporated into a consumer product. Similarly, the reaction mixture comprising the microcapsules of the invention may be sprayed onto a dry, powdered product, such as a washing powder or powdered detergent or the microcapsules may be dried and added to these products in solid form. The microcapsules may for example be spray-dried.

Preferably, the consumer product comprises from 0.01 to 10%, more preferably from 0.05 to 2% of the microcapsules of the present invention, these percentages being defined by weight relative to the total weight of the consumer product. Of course the above concentrations may be adapted according to the olfactive effect desired in each product.

Formulations of consumer product bases in which the microcapsules of the invention can be incorporated can be found in the abundant literature relative to such products. These formulations do not warrant a detailed description here, which would in any case not be exhaustive. The person skilled in the art of formulating such consumer products is perfectly able to select the suitable components on the basis of his general knowledge and of the available literature. In particular, examples of such formulations can be found in the patents and patent applications relative to such products, for example in WO 2008/016684 (pages 10 to 14), in US 2007/0202063 (paragraphs [0044] to [0099]), in WO 2007/062833 (pages 26 to 44), in WO 2007/062733 (pages 22 to 40), in WO 2005/054422 (pages 4 to 9), in EP 1741775, in GB 2432843, in GB 2432850, in GB 2432851 or in GB 2432852.

EXAMPLES

Figure 1:
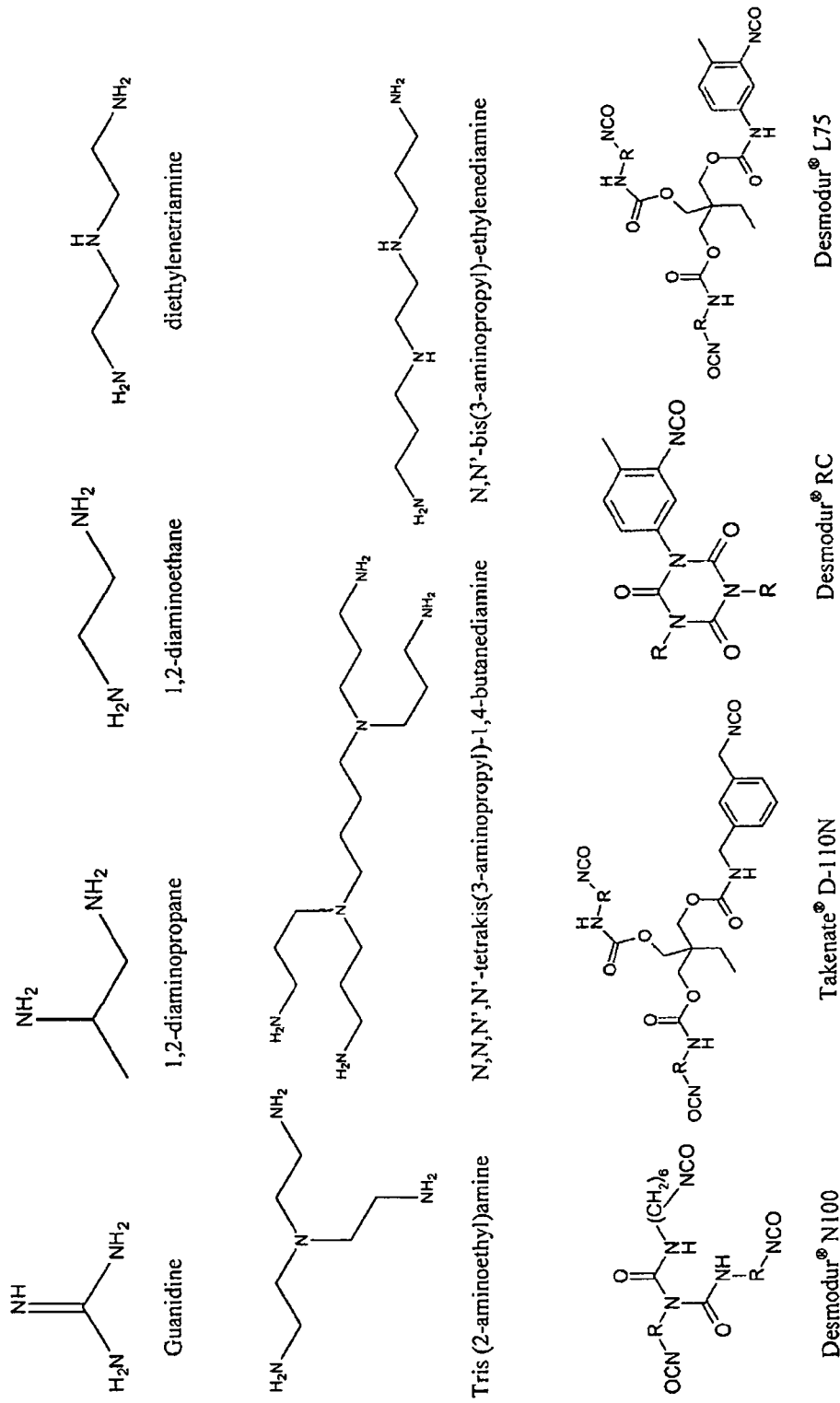
FIG. 1: Chemical structures of some polyamines and polyisocyanates that can be used in the present invention.

The following examples are further illustrative of the present invention embodiments, and further demonstrate the advantages of the invention devices relative to prior art teachings.

Example 1

Preparation of Polyurea Microcapsules of the Invention

Polyurea microcapsules according to the invention (Capsules A) were prepared having the following ingredients:

TABLE 1

Composition of Capsules A

| Ingredient | Amount [g] | Molar percentage, relative to total polyisocyanate |
|---|---|---|
| Desmodur® N 100[1] | 21.4 | 80 |
| Takenate® D-110N[2] | 10.2 | 20 |
| Perfume[3] | 400.0 | |
| Polyvinyl alcohol[4] | 5.5 | |
| Tetraethyl ammonium chloride[5] | 4.0 | |
| Guanidine carbonate[6] | 9.0 | |
| Water | 562.5 | |

[1] Biuret of hexamethylene diisocyanate, origin: Bayer
[2] Trimethylol propane-adduct of xylylene diisocyanate, origin: Mitsui Chemicals
[3] Perfuming composition having the ingredients of Table 1a
[4] Mowiol® 18-88, origin: Fluka
[5] Tetraethyl ammonium chloride (50% aqueous solution), origin: Fluka
[6] Origin: Acros Organics TABLE 1a Composition of the perfume

| Ingredient | LogP | Amount [%] |
|---|---|---|
| Allyl (cyclohexyloxy)-acetate[a] | 2.72 | 1.2 |
| 2,4-Dimethyl-3-cyclohexene-1-carbaldehyde[b] | 2.85 | 1.2 |
| Menthone | 2.87 | 1.7 |
| Hedione®[c] | 2.98 | 5.8 |
| Camphor | 3.04 | 2.9 |
| Eucalyptol | 3.13 | 5.8 |
| Dihydromyrcenol[d] | 3.47 | 11.5 |
| Rose oxyde | 3.58 | 0.9 |
| Isobornyl acetate | 3.86 | 11.5 |
| Delta damascone | 4.13 | 0.6 |
| Cashmeran®[e] | 4.31 | 2.3 |
| Terpenyl acetate | 4.34 | 5.8 |
| Lilial®[f] | 4.36 | 17 |
| Linalyl acetate | 4.39 | 2.3 |
| Neobutenone® alpha[g] | 4.45 | 1.2 |
| Dihydromyrcenyl acetate | 4.47 | 2.3 |
| 2-Methylundecanal | 4.67 | 3.5 |
| Iso E Super®[h] | 4.71 | 11.5 |
| Cetalox®[i] | 4.76 | 0.6 |
| Isoraldeine® 70[j] | 4.84 | 2.3 |
| Habanolide®[k] | 4.88 | 4.6 |
| Precyclemone B[l] | 5.18 | 3.5 |
| Total | | 100.0 |

[a] Origin: Dragoco, Holzminden, Germany
[b] Origin: Firmenich SA, Geneva, Switzerland
[c] Methyl dihydrojasmonate, origin: Firmenich SA, Geneva, Switzerland
[d] Origin: International Flavors & Fragrances, USA
[e] 1,2,3,5,6,7-Hexahydro-1,2,3,3-pentamethyl-4h-inden-4-one, origin: International Flavors & Fragrances, USA
[f] 3-(4-Tert-butylphenyl)-2-methylpropanal, origin: Givaudan SA, Vernier, Switzerland
[g] 1-(5,5-Dimethyl-1-cyclohexen-1-yl)-4-penten-1-one, origin: Firmenich SA, Geneva, Switzerland
[h] 1-(Octahydro-2,3,8,8-tetramethyl-2-naphtalenyl)-1-ethanone, origin: International Flavors & Fragrances, USA
[i] Dodecahydro-3a,6,6,9a-tetramethyl-naphtho[2,1-b]furan, origin: Firmenich SA, Geneva, Switzerland
[j] 3-Methyl-4-(2,6,6-trimethyl-2cyclohexen-1-yl)-3-buten-2-one, origin: Givaudan SA, Vernier, Switzerland
[k] Pentadecenolide, origin: Firmenich SA, Geneva, Switzerland
[l] 1-Methyl-4-(4-methyl-3-pentenyl)cyclohex-3-ene-1-carboxaldehyde, origin: International Flavors & Fragrances, USA The Desmodur® N 100 and the Takenate D-110N were dissolved in the perfume. This oil phase was introduced in a one litre glass double-jacketed reactor equipped with a scrapped stirrer and an Ika-rotor/stator system (6500-24000 rpm). The oil phase was stirred at 50 rpm with the scrapped stirrer for 5 minutes.

An aqueous stabilizer solution at 1% by weight, relative to the total weight of the stabilizer solution, was prepared by dissolving the polyvinyl alcohol in 543.5 g of deionised water. This solution was introduced into the reactor at room temperature and the scrapped stirrer was stopped.

A pre-emulsion was then prepared by dispersing the perfume phase in the aqueous phase with the Ika-rotor/stator system during 10 minutes at 13500 rpm.

Once the emulsion was prepared, the stirring was continued with the scrapped stirrer at 200 rpm until the end of the process.

The tetraethyl ammonium chloride solution was added to the emulsion. Then, a solution of the guanidine carbonate in 19 g of deionised water was added to the reactor over one hour. The temperature of the reaction mixture was then slowly increased over one hour from room temperature to 70° C. The temperature was then kept at 70° C. for two hours. The stirring speed was then decreased to 100 rpm and the capsules suspension was cooled down to room temperature.

The perfume content in the capsules suspension was around 40%, relative to the total weight of the suspension.

Example 2

Preparation of Polyurea Microcapsules of the Invention

Capsules B to G were prepared using the method described in Example 1. There were used the same amounts of perfume, polyvinyl alcohol, tetraethyl ammonium chloride, guanidine carbonate and water, as in Table 1. Only the amounts of Desmodur® N 100 and Takenate® 110N varied, as indicated in the table below.

TABLE 2

Amounts of polyisocyanates in Capsules B to G

|  | Desmodur® N 100[1] | | Takenate® D-110N[2] | |
|---|---|---|---|---|
|  | Amount [g] | Mol %, relative to total polyisocyanate | Amount [g] | Mol %, relative to total polyisocyanate |
| Capsules B | 20.0 | 75 | 12.8 | 25 |
| Capsules C | 16.0 | 60 | 20.5 | 40 |
| Capsules D | 13.4 | 50 | 25.6 | 50 |
| Capsules E | 12.0 | 45 | 28.1 | 55 |
| Capsules F | 10.7 | 40 | 30.7 | 60 |
| Capsules G | 9.4 | 35 | 33.2 | 65 |

[1] Biuret of hexamethylene diisocyanate, origin: Bayer
[2] Trimethylol propane-adduct of xylylene diisocyanate, origin: Mitsui Chemicals Example 3

Preparation of Polyurea Microcapsules of the Invention

Capsules H and I were prepared using the method described in Example 1. There were used the same amounts of perfume, polyvinyl alcohol, tetraethyl ammonium chloride, guanidine carbonate and water, as in Table 1. Only the nature and the amount of the polyisocyanate varied. Takenate® D-110N was replaced by Desmodur® RC in Capsules H and by Desmodur® L75 in Capsules I. The respective amounts of polyisocyanate used in Capsules H and I are summarized in the two tables below.

TABLE 3

Amount of polyisocyanates in Capsules H

|  | Desmodur® N 100[1] | | Desmodur® RC[2] | |
|---|---|---|---|---|
|  | Amount [g] | Mol %, relative to total polyisocyanate | Amount [g] | Mol %, relative to total polyisocyanate |
| Capsules H | 21.4 | 80 | 16.8 | 20 |

[1] Biuret of hexamethylene diisocyanate, origin: Bayer
[2] Polyisocyanurate of toluene diisocyanate, origin: Bayer

TABLE 4

Amount of polyisocyanates in Capsules I

|  | Desmodur® N 100[1] | | Desmodur® L75[2] | |
|---|---|---|---|---|
|  | Amount [g] | Mol %, relative to total polyisocyanate | Amount [g] | Mol %, relative to total polyisocyanate |
| Capsules I | 21.4 | 80 | 8.8 | 20 |

[1] Biuret of hexamethylene diisocyanate, origin: Bayer
[2] Trimethylol propane of toluene diisocyanate, origin: Bayer Example 4

Preparation of Polyurea Microcapsules of the Invention

Polyurea microcapsules according to the invention (Capsules J) were prepared having the following ingredients.

TABLE 5

Composition of Capsules J

| Ingredient | Amount [g] | Molar percentage, relative to total polyisocyanate |
|---|---|---|
| Desmodur® N 100[1] | 12.0 | 45 |
| Takenate® D-110N[2] | 28.1 | 55 |
| Perfume[3] | 400.0 | — |
| Polyvinyl alcohol[4] | 5.5 | — |
| Tetraethyl ammonium chloride[5] | 4.0 | — |
| Guanidine carbonate[6] | 9.0 | — |
| Water | 562.5 |  |

[1] Biuret of hexamethylene diisocyanate, origin: Bayer
[2] Trimethylol propane-adduct of xylylene diisocyanate, origin: Mitsui Chemicals
[3] Perfuming composition of Table 1a (as in Example 1)
[4] Mowiol® 18-88, origin: Fluka
[5] Tetraethyl ammonium chloride (50% aqueous solution), origin: Fluka
[6] Origin: Acros Organics The Desmodur® N 100 and the Takenate® D-110N were dissolved in the perfume. This oil phase was introduced in a one litre glass double-jacketed reactor equipped with a scrapped stirrer and an Ika-rotor/stator system. (6500-24000 rpm). The oil phase was stirred at 50 rpm with the scrapped stirrer for 5 minutes.

An aqueous stabilizer solution at 1% by weight, relative to the total weight of the stabilizer solution, was prepared by dissolving the polyvinyl alcohol in 543.5 g of deionised water. This solution was introduced into the reactor at room temperature and the scrapped stirrer was stopped.

A pre-emulsion was then prepared by dispersing the perfume phase in the aqueous phase with the Ika-rotor/stator system during 10 minutes at 13500 rpm.

Once the emulsion was prepared, the stirring was continued with the scrapped stirrer at 200 rpm till the end of the process.

The tetraethyl ammonium chloride solution was added to the emulsion. Then, a solution of the guanidine carbonate in 19 g of deionised water was added to the reactor over one hour. The temperature of the reaction mixture was kept at room temperature for two hours.

The perfume content in the capsules suspension was around 40%, relative to the total weight of the suspension.

Example 5

Preparation of Polyurea Microcapsules of the Invention

Capsules K, L and M were prepared using the method described in Example 4. There were used the same amounts of perfume, polyvinyl alcohol, tetraethyl ammonium chloride, Desmodur® N 100, Takenate® D-110N and water, as in Table 5. Only the nature and the amount of the polyamine used varied, as summarized in the following table.

TABLE 6

Polyamines used in Capsules K, L and M

| | Polyamine | Amount [g] |
|---|---|---|
| Capsules K | 1,2-Diaminopropane[1] | 7.4 |
| Capsules L | 1,2-Diaminoethane[1] | 6.0 |
| Capsules M | Diethylenetriamine[1] | 10.3 |

[1] Origin: Fluka

Example 6

Preparation of Polyurea Microcapsules of the Invention

Capsules N to P were prepared using the method described in Example 4, except that 6.8 g of tris(2-aminoethyl)amine (origin: Fluka) were used as polyamine. The respective amount of Desmodur® N 100 and Takenate® D-110N varied for each of these capsules as summarized in the table below.

TABLE 7

Amounts of polyisocyanates in Capsules N to P

| | Desmodur® N 100[1] | | Takenate® D-110N[2] | |
|---|---|---|---|---|
| | Amount [g] | Mol %, relative to total polyisocyanate | Amount [g] | Mol %, relative to total polyisocyanate |
| Capsules N | 12 | 45 | 28.1 | 55 |
| Capsules O | 8 | 30 | 35.8 | 70 |
| Capsules P | 5.3 | 20 | 40.9 | 80 |

[1] Biuret of hexamethylene diisocyanate, origin: Bayer
[2] Trimethylol propane-adduct of xylylene diisocyanate, origin: Mitsui Chemicals

Example 7

Preparation of Polyurea Microcapsules of the Invention

Capsules Q to S were prepared using the method described in Example 4, except that 11.1 g of N,N,N',N'-tetrakis(3-aminopropyl)-1,4-butanediamine (DAB-Am-4, origin: Sigma-Aldrich) were used as polyamine. The respective amount of Desmodur® N 100 and Takenate® D-110N varied for each of these capsules, as summarized in the table below.

TABLE 8

Amounts of polyisocyanates in Capsules Q to S

| | Desmodur® N 100[1] | | Takenate® D-110N[2] | |
|---|---|---|---|---|
| | Amount [g] | Mol %, relative to total polyisocyanate | Amount [g] | Mol %, relative to total polyisocyanate |
| Capsules Q | 12 | 45 | 28.1 | 55 |
| Capsules R | 8 | 30 | 35.8 | 70 |
| Capsules S | 5.3 | 20 | 40.9 | 80 |

[1] Biuret of hexamethylene diisocyanate, origin: Bayer
[2] Trimethylol propane-adduct of xylylene diisocyanate, origin: Mitsui Chemicals

Example 8

Preparation of Polyurea Microcapsules of the Invention

Capsules T and U were prepared using the method described in Example 4, except that 12.2 g of N,N'-bis(3-aminopropyl)-ethylenediamine (origin: Acros Organics) were used as polyamine. The respective amount of Desmodur® N 100 and Takenate® D-110N varied for each of these capsules, as summarized in the table below.

TABLE 9

Amounts of polyisocyanates in Capsules T and U

| | Desmodur® N 100[1] | | Takenate® D-110N[2] | |
|---|---|---|---|---|
| | Amount [g] | Mol %, relative to total polyisocyanate | Amount [g] | Mol %, relative to total polyisocyanate |
| Capsules T | 12 | 45 | 28.1 | 55 |
| Capsules U | 8 | 30 | 35.8 | 70 |

[1] Biuret of hexamethylene diisocyanate, origin: Bayer
[2] Trimethylol propane-adduct of xylylene diisocyanate, origin: Mitsui Chemicals

Example 9 (Comparative)

Preparation of Polyurea Microcapsules Comprising Only an Aliphatic Polyisocyanate Comparative capsules (Control A) were prepared using an aliphatic polyisocyanate alone. The capsules have the following ingredients:

TABLE 10

Composition of Control A

| Ingredient | Amount [g] |
|---|---|
| Desmodur® N 100[1] | 26.7 |
| Guanidine carbonate[2] | 9.0 |
| Perfume[3] | 400.0 |
| Polyvinyl alcohol[4] | 5.5 |
| Tetraethyl ammonium chloride[5] | 4.0 |
| Water | 562.5 |

[1] Biuret of hexamethylene diisocyanate, origin: Bayer
[2] Origin: Acros Organics
[3] Perfuming composition of Table 1a (as in Example 1)
[4] Mowiol® 18-88, origin: Fluka
[5] Tetraethyl ammonium chloride (50% aqueous solution), origin: Fluka These capsules were prepared using the method described in Example 1.

Example 10 (Comparative)

Preparation of Polyurea Microcapsules Comprising Only an Aliphatic Polyisocyanate Controls B to G and L were prepared according to the method of Example 4. The amounts of Desmodur® N 100, perfume, polyvinyl alcohol, tetraethyl ammonium chloride and water used were those indicated in Table 10. Only the nature and the amount of the polyamine used varied, as indicated in the following table.

TABLE 11

Composition of Controls B to G and L

| | Polyamine | Amount [g] |
|---|---|---|
| Control B | Guanidine Carbonate[1] | 9.0 |
| Control C | 1,2-Diaminopropane[2] | 7.4 |
| Control D | 1,2-Diaminoethane[2] | 6.0 |
| Control E | Diethylenetriamine[2] | 10.3 |

TABLE 11-continued

Composition of Controls B to G and L

| | Polyamine | Amount [g] |
|---|---|---|
| Control F | Tris (2-aminoethyl)amine[2] | 6.8 |
| Control G | N,N,N',N'-tetrakis(3-amino-propyl)-1,4-butanediamine[3] | 11.1 |
| Control L | N,N'-bis(3-amino-propyl)-ethylenediamine[4] | 12.2 |

[1] Origin: Acros Organics
[2] Origin: Fluka
[3] DAB-Am-4, origin: Sigma-Aldrich
[4] Origin: Acros Organics

Example 11 (Comparative)

Preparation of Polyurea Microcapsules Comprising Only an Aromatic Polyisocyanate Comparative capsules (Control H) were prepared using an aromatic polyisocyanate alone. These capsules have the following ingredients:

TABLE 12

Composition of Control H

| Ingredient | Amount [g] |
|---|---|
| Takenate® D-110N[1] | 51.1 |
| Perfume[2] | 400 |
| Polyvinyl alcohol[3] | 5.5 |
| Tetraethyl ammonium chloride[4] | 4 |
| Guanidine carbonate[5] | 9 |
| Water | 562.5 |

[1] Trimethylol propane-adduct of xylylene diisocyanate, origin: Mitsui Chemicals
[2] Perfuming composition of Table 1a (as in Example 1)
[3] Mowiol® 18-88, origin: Fluka
[4] Tetraethyl ammonium chloride (50% aqueous solution), origin: Fluka
[5] Origin: Acros Organics These capsules were prepared using the method described in Example 1.

Example 12 (Comparative)

Preparation of Polyurea Microcapsules Comprising Only an Aromatic Polyisocyanate Controls I to K and M were prepared according to the method of Example 4. The amounts of Takenate® D-110N, perfume, polyvinyl alcohol, tetraethyl ammonium chloride and water used were those indicated in Table 12. Only the nature and the amount of the polyamine used varied in Controls I to K and M, as summarized in the following table.

TABLE 13

Composition of Controls I to K and M

| | Polyamine | Amount [g] |
|---|---|---|
| Control I | Diethylenetriamine[1] | 10.3 |
| Control J | Tris (2-aminoethyl)amine[2] | 6.8 |

TABLE 13-continued

Composition of Controls I to K and M

| | Polyamine | Amount [g] |
|---|---|---|
| Control K | N,N,N',N'-tetrakis(3-amino-propyl)-1,4-butanediamine[2] | 11.1 |
| Control M | N,N'-bis(3-amino-propyl)-ethylenediamine[3] | 12.2 |

[1] Origin: Fluka
[2] DAB-Am-4, origin: Sigma-Aldrich
[3] Origin: Acros Organics

Example 13

Average Diameter of the Capsules of the Invention

The size distribution of the Capsules A to U was controlled by Optical Microscopy and Light Scattering (Mastersizer S, Malvern) and the average diameter was calculated (arithmetic mean) for each type of capsules. The results are summarized in the following table.

TABLE 14

Average diameter of Capsules A to U

| Capsules of the invention | Average diameter d(v, 0.5) [μm] |
|---|---|
| Capsules A | 5 |
| Capsules B | 5 |
| Capsules C | 5 |
| Capsules D | 5 |
| Capsules E | 6 |
| Capsules F | 5 |
| Capsules G | 5 |
| Capsules H | 7 |
| Capsules I | 5 |
| Capsules J | 5 |
| Capsules K | 5 |
| Capsules L | 5 |
| Capsules M | 9 |
| Capsules N | 7 |
| Capsules O | 8 |
| Capsules P | 9 |
| Capsules Q | 7 |
| Capsules R | 9 |
| Capsules S | 5 |
| Capsules T | 7 |
| Capsules U | 6 |

Example 14

Preparation of a Fabric Softener Comprising the Polyurea Microcapsules of the Invention A concentrated unperfumed fabric softener base was prepared by admixing the ingredients listed in Table 15, in the amounts indicated. The percentages are defined by weight relative to the total weight of the unperfumed fabric softener base.

TABLE 15

Formulation of the concentrated unperfumed fabric softener base

| Ingredient | % |
|---|---|
| Stepantex VL90 A Diester Quat[1] | 16.50 |
| Proxel GXL[2] | 0.04 |
| CaCl$_2$ (10% aqueous solution) | 0.20 |
| Water | 83.26 |

[1]Origin: Stepan
[2]Origin: Avecia

Softeners A to U were prepared by adding Capsules A to U at 1.26% by weight, relative to the total weight of the softener, under gentle shaking into the unperfumed softener base of Table 15.

Example 15 (Comparative)

Preparation of a Fabric Softener Comprising the Polyurea Microcapsules of Examples 9 to 12

Control Softeners A to M were prepared by adding Controls A to M at 1.25% by weight, relative to the total weight of the softener, under gentle shaking into the unperfumed softener base prepared in Example 14.

Example 16

Stability of the Polyurea Microcapsules of the Invention in a Fabric Softener Base The storage stability of the capsules in Softeners A to U and in Control Softeners A to G and L was evaluated. The softeners comprising the capsules were stored during one month at 38° C. and the amount of perfume having leaked out of the capsules was measured by solvent extraction and GC-MS analysis.

The results are summarized in the following table.

TABLE 16

Storage stability of the capsules in Softeners A to U and Control Softeners A to G and L

| Fabric softener of the invention | Amount of perfume that leaked out of the capsules [%] | Amount of perfume that leaked out of the control capsules [%] | Corresponding control fabric softener |
|---|---|---|---|
| Softener A | 20.6 | 49 | Control A |
| Softener B | 14.4 | | |
| Softener C | 6.4 | | |
| Softener D | 4.7 | | |
| Softener E | 3.9 | | |
| Softener F | 3.6 | | |
| Softener G | 3.4 | | |
| Softener H | 35.0 | | |
| Softener I | 26.0 | | |
| Softener J | 7.0 | 64 | Control B |
| Softener K | 48.0 | 100 | Control C |
| Softener L | 49.0 | 100 | Control D |
| Softener M | 37.0 | 100 | Control E |
| Softener N | 43.0 | 100 | Control F |
| Softener O | 22.0 | | |
| Softener P | 17.0 | | |
| Softener Q | 25.0 | 100 | Control G |
| Softener R | 15.0 | | |
| Softener S | 11.0 | | |
| Softener T | 18.0 | 100 | Control L |
| Softener U | 10.0 | | |

It is apparent from these results that each of the capsules of the present invention was more stable in the softener base than the corresponding control, in which only the aliphatic polyisocyanate was used, thus showing that combining an aromatic polyisocyanate with an aliphatic polyisocyanate in the claimed ratios improves the storage stability of polyurea microcapsules in a fabric softener base.

Figure 2:
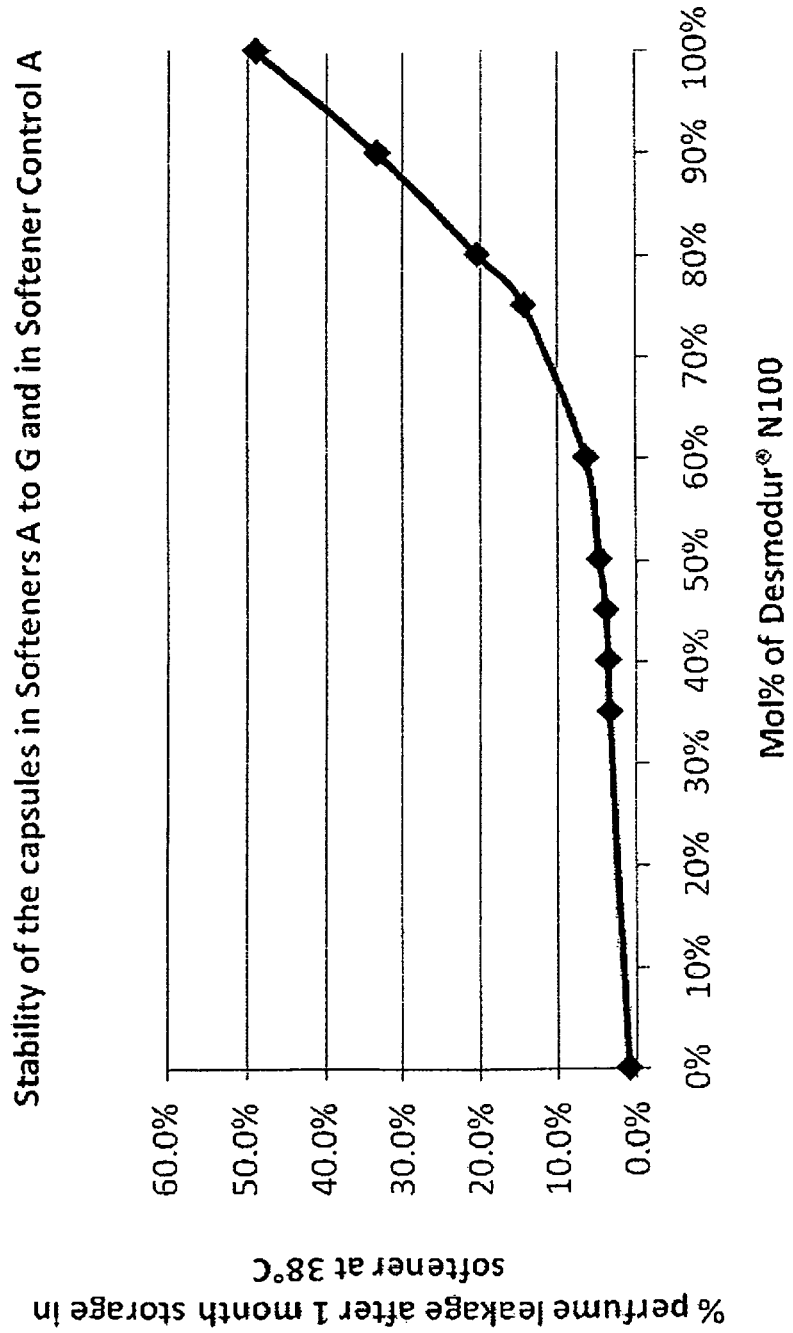
FIG. 2: Graph representing the stability of the capsules of the invention in Softeners A to G and Control Softener A as a function of the proportion (mol %) of aliphatic polyisocyanate (Desmodur® N 100) in the Desmodur® N 100/Takenate® D-110N mixture used to prepare the capsules.

In order to further illustrate these results, the stability of the capsules in Softeners A to G and in Control Softener A is represented in FIG. 2. It is clear from this graph that the stability of the capsules is clearly improved by mixing an aromatic polyisocyanate such as Takenate® to D-110N with the aliphatic polyisocyanate in all claimed ratios.

Example 17

Olfactive Performance of the Polyurea Microcapsules of the Invention in a Fabric Softener The olfactive performance of Capsules B, C, E, G, T and U as well of that of Controls A, H, L and M was then evaluated in the corresponding fabric-softeners of Examples 14 and 15. Cotton terry towels (20 pieces, 18 cm*18 cm, about 30 g each) were washed with 30 g of unperfumed detergent in a washing machine (Miele Novotronic W300-33CH) at 40° C. using the short cycle program. The wash was followed by a rinse at 900 rpm with 12.7 g of the Softeners or Control Softeners. The terry towels were then line dried for 24 hours before being evaluated.

The intensity of the perception of the perfume on the dry towels treated with Softeners B, C, E and G and with Control Softeners A and H was evaluated by a panel of 20 trained panelists. They were asked to rub the towels in their hands and then to rate the intensity of the perfume perception on a scale ranging from 1 to 7, wherein 1 means no odour and 7 means very strong odour. The intensity of the perception of the perfume on the dry towels treated with Softeners T and U and with Control Softeners L and M was evaluated according to the same method by a panel of 10 trained panelists, using the same scale. The results are summarized in the following table.

TABLE 17

Olfactive performance of Capsules B, C, E, G, T and U and of Controls A, H, M and L in a fabric softener

| Capsule of the invention | Olfactive performance of the capsules of the invention | Olfactive performance of the Control | Corresponding control |
|---|---|---|---|
| Capsules B | 4.75 | 3.80 | Control A |
| | | 3.80 | Control H |
| Capsules C | 4.90 | 3.80 | Control A |
| | | 3.80 | Control H |
| Capsules E | 4.90 | 3.80 | Control A |
| | | 3.80 | Control H |
| Capsules G | 4.90 | 3.80 | Control A |
| | | 3.80 | Control H |
| Capsules T | 5.10 | 2.00 | Control L |
| | | 4.10 | Control M |
| Capsules U | 4.30 | 2.00 | Control L |
| | | 4.10 | Control M |

The assessment of the intensity of the perception of the perfume on the dry towels treated with Softeners M to S and with Control Softeners E to G and I to K was carried out as described above, except that the panelists were asked to rate the intensity of the perfume perception on a scale ranging from 0 to 10, wherein 0 means no odour and 10 means very strong odour. The results are summarized in the following table.

TABLE 18

Olfactive performance of Capsules M to S and of Controls E to G and I to K in a fabric softener

| Capsule of the invention | Olfactive performance of the capsules of the invention | Olfactive performance of the Control | Corresponding control |
|---|---|---|---|
| Capsules M | 3.50 | 2.00 | Control E |
| | | 2.70 | Control I |
| Capsules N | 6.10 | 2.25 | Control F |
| | | 5.20 | Control J |
| Capsules O | 6.10 | 2.25 | Control F |
| | | 5.20 | Control J |
| Capsules P | 5.50 | 2.00 | Control F |
| | | 5.20 | Control J |
| Capsules Q | 6.90 | 3.25 | Control G |
| | | 5.20 | Control K |
| Capsules R | 6.00 | 3.25 | Control G |
| | | 5.20 | Control K |
| Capsules S | 5.50 | 3.25 | Control G |
| | | 5.20 | Control K |

These results show that the intensity of the perfume's odour was perceived stronger on the fabric treated with a softener comprising the capsules of the present invention than with both controls. Therefore, the perfume is perceived more intensely when the capsules are made with a combination of an aromatic and an aliphatic polyisocyanate in the claimed ratios than when the capsules are made with an aromatic polyisocyanate alone or with an aliphatic polyisocyanate alone.

Example 18

Preparation of a Concentrated Liquid Detergent Comprising the Polyurea Microcapsules of the Invention Liquid Detergents E, G, T and U were prepared by mixing Capsules E, G, T and U at 0.275% by weight, relative to the total weight of the detergent with the commercially available unperfumed concentrated liquid detergent base Tide® 2×HE Free of perfume and dye (trademark of Procter and Gamble, USA).

Example 19 (Comparative)

Preparation of a Concentrated Liquid Detergent Comprising the Polyurea Microcapsules of Examples 9 to 12

Control Liquid Detergents A, H, L and M were prepared by mixing Controls A, H, L and M at 0.275% by weight, relative to the total weight of the detergent with the commercially available unperfumed concentrated liquid detergent base Tide® 2×HE Free of perfume and dye (trademark of Procter and Gamble, USA).

Example 20

Olfactive Performance of the Polyurea Microcapsules of the Invention in Concentrated Liquid Detergent The olfactive performance of Capsules E, G, T and U as well as that of Controls A, H, L and M was then evaluated in the corresponding concentrated liquid detergents of Examples 18 and 19.

Fabrics (2.5 kg of cotton terry towels) were washed at 40° C. in a standard European horizontal axis machine. There were dispensed 80 g of freshly prepared detergent at the start of the wash through the detergent drawer. After the wash, fabrics were line-dried and the odour intensity of the cotton towels was evaluated by a panel of 20 trained panelists, after 1 day drying. The panelists were asked to rate the odour intensity of the towels after gentle rubbing of the fabrics by hand on a scale from 1 to 7, 1 corresponding to odorless and 7 corresponding to a very strong odour. The results are shown in Table 19.

TABLE 19

Olfactive performance of Capsules E, G, T and U and of Controls A, H, L and M in concentrated liquid detergent

| Capsule of the invention | Olfactive performance of the capsules of the invention | Olfactive performance of the Control | Corresponding control |
|---|---|---|---|
| Capsules E | 4.20 | 2.90 | Control A |
| | | 2.90 | Control H |
| Capsules G | 3.60 | 2.90 | Control A |
| | | 2.90 | Control H |
| Capsules T | 4.70 | 4.00 | Control L |
| | | 3.50 | Control M |
| Capsules U | 4.50 | 4.00 | Control L |
| | | 3.50 | Control M |

It is clear from these results that, after rubbing, the perfume intensity was more intense on fabrics washed with the liquid detergent containing the capsules of the invention, than on fabrics washed with the liquid detergent containing the control capsules.

Therefore, the perfume is perceived more intensely when the capsules are made with a combination of an aromatic and an aliphatic polyisocyanate in the claimed ratios than when the capsules are made with an aromatic polyisocyanate alone or with an aliphatic polyisocyanate alone.

Example 21

Stability of the Polyurea Microcapsules of the Invention in a Concentrated Liquid Detergent The storage stability of the capsules in Liquid Detergents E, G, T and U and in Control Liquid Detergents A and L was evaluated. The detergents comprising the capsules were stored during four weeks at 38° C. and the amount of perfume having leaked out of the capsules was measured by solvent extraction and GC-MS analysis.

The results are summarized in the following table.

TABLE 20

Storage stability of the capsules of the invention in Liquid Detergents E, G, T and U and in Control Liquid Detergents A and L.

| Liquid Detergent of the invention | Amount of perfume that leaked out of the capsules [%] | Amount of perfume that leaked out of the control capsules [%] | Corresponding Liquid Detergent control |
|---|---|---|---|
| Liquid Detergent E | 4 | 47 | Control A |
| Liquid Detergent G | 3 | | |
| Liquid Detergent T | 27 | 100 | Control L |
| Liquid Detergent U | 18 | | |

It is apparent from these results that each of the capsules of the present invention was more stable in the concentrated liquid detergent base than the corresponding control, in which only the aliphatic polyisocyanate was used, thus showing that combining an aromatic polyisocyanate with an aliphatic polyisocyanate in the claimed ratios improves the storage stability of polyurea microcapsules in a concentrated liquid detergent base.

Example 22

Preparation of a Concentrated Powder Detergent Comprising the Polyurea Microcapsules of the Invention Powder Detergents E, G, T and U were prepared by mixing Capsules E, G, T and U at 0.275% by weight, relative to the total weight of the detergent into the commercially available unperfumed concentrated powder detergent base Ultra Tide® Free and Gentle (trademark of Procter and Gamble, USA).

Example 23 (Comparative)

Preparation of a Concentrated Powder Detergent Comprising the Polyurea Microcapsules of Examples 9 to 12

Control Powder Detergents A, H, L and M were prepared by adding Controls A, H, L and M at 0.275% by weight, relative to the total weight of the detergent into the commercially available unperfumed concentrated powder detergent base Ultra Tide® Free and Gentle (trademark of Procter and Gamble, USA).

Example 24

Olfactive Performance of the Polyurea Microcapsules of the Invention in Concentrated Powder Detergent The olfactive performance of Capsules E, G, T and U as well as that of Controls A, H, L and M was then evaluated in the corresponding concentrated powder detergents of Examples 22 and 23.

Fabrics (2.5 kg of cotton terry towels) were washed at 40° C. in a standard European horizontal axis machine. There were dispensed 50 g of freshly prepared detergent at the start of the wash through the detergent drawer. After the wash, fabrics were line-dried and the odour intensity of the cotton towels was evaluated by a panel of 20 trained panelists, after 1 day drying. The panelists were asked to rate the odour intensity of the towels after gentle rubbing of the fabrics by hand on a scale from 1 to 7, 1 corresponding to odorless and 7 corresponding to a very strong odour. The results are shown in Table 21.

TABLE 21

Olfactive performance of Capsules E, G, T and U and of Controls A, H, L and M in concentrated powder detergent

| Capsule of the invention | Olfactive performance of the capsules of the invention | Olfactive performance of the Control | Corresponding control |
| --- | --- | --- | --- |
| Capsules E | 4.20 | 3.00 | Control A |
|  |  | 2.90 | Control H |
| Capsules G | 3.80 | 3.00 | Control A |
|  |  | 2.90 | Control H |
| Capsules T | 4.60 | 3.90 | Control L |
|  |  | 3.70 | Control M |
| Capsules U | 4.40 | 3.90 | Control L |
|  |  | 3.70 | Control M |

It is clear from these results that, after rubbing, the perfume intensity was more intense on fabrics washed with the concentrated powder detergent containing the capsules of the invention, than on fabrics washed with the concentrated powder detergent containing the control capsules.

Therefore, the perfume is perceived more intensely when the capsules are made with a combination of an aromatic and an aliphatic polyisocyanate in the claimed ratios than when the capsules are made with an aromatic polyisocyanate alone or with an aliphatic polyisocyanate alone.

Example 25

Preparation of a Body Wash Comprising the Polyurea Microcapsules of the Invention A body wash formulation was prepared by admixing the ingredients listed in Table 22, in the amounts indicated. The percentages are defined by weight relative to the total weight of the body wash formulation.

TABLE 22

Composition of the body wash formulation

| Ingredient | Amount [%] w/w |
| --- | --- |
| Carbopol ® Aqua CC polymer[1] | 8.0 |
| Citric acid (40% solution in water) | 0.5 |
| Zetesol AO 328 U[2] | 25.0 |
| Tego Betain F 50[3] | 4.0 |
| Glydant Plus Liquid[4] | 0.1 |
| Sodium Chloride (20% solution in water) | 4.0 |
| Water | 58.4 |

[1]Polyacrylate-1 crosspolymer, origin: Noveon
[2]Sodium $C_{12}$-$C_{15}$ pareth sulfate, origin: Zschimmer & Schwarz
[3]Cocamidopropyl betaine, origin: Goldschmidt AG
[4]DMDM hydantoin and iodopropynyl butylcarbamate, origin: Lonza Body Washes E, G, T and U were prepared by mixing Capsules E, G, T and U at 0.5% by weight, relative to the total weight of the body wash into the body wash formulation prepared above.

Example 26 (Comparative)

Preparation of a Body Wash Comprising the Polyurea Microcapsules of Examples 9 to 12

Control Body Washes A, H, L and M were prepared by adding Controls A, H, L and M at 0.5% by weight, relative to the total weight of the body wash into the body wash formulation prepared in Example 25.

Example 27

Olfactive Performance of the Polyurea Microcapsules of the Invention in Body Wash The olfactive performance of Capsules E, G, T and U as well as that of Controls A, H, L and M was then evaluated in the corresponding body washes of Examples 25 and 26.

Body Washes were applied to wool swatches intended to mimic human skin. The wool swatches were wetted during 30 s under running water at 38° C. The Body Washes were then respectively applied in an amount of 0.5 g with a micropipette and lather was then created during 10 s by rubbing a finger on the whole surface. The swatches were then rinsed during 20 s under running water at 38° C. and finally allowed to dry on a hotplate at 32° C.

The perfume intensity was then evaluated on a blind basis by an expert panel consisting of 4 trained panelists who were asked to rate the perceived perfume intensity on the wool swatches after rubbing with the hand, on a scale ranging from 1 to 7, wherein 1 means no odour and 7 means very strong odour. The results are summarized in Table 23.

TABLE 23

Olfactive performance of Capsules E, G, T and U and of Controls A, H, L and M in body wash

| Capsule of the invention | Olfactive performance of the capsules of the invention | Olfactive performance of the Control | Corresponding control |
|---|---|---|---|
| Capsules E | 7.00 | 3.00 | Control A |
|  |  | 4.30 | Control H |
| Capsules G | 6.00 | 3.00 | Control A |
|  |  | 4.30 | Control H |
| Capsules T | 6.00 | 4.60 | Control L |
|  |  | 5.00 | Control M |
| Capsules U | 6.60 | 4.60 | Control L |
|  |  | 5.00 | Control M |

It is clear from these results that, after rubbing, the perfume intensity was more intense on wool swatches washed with the body wash containing the capsules of the invention, than on wool swatches washed with the body wash containing the control capsules.

Therefore, the perfume is perceived more intensely when the capsules are made with a combination of an aromatic and an aliphatic polyisocyanate in the claimed ratios than when the capsules are made with an aromatic polyisocyanate alone or with an aliphatic polyisocyanate alone.

Example 28

Stability of the Polyurea Microcapsules of the Invention in a Body Wash

The storage stability of the capsules in Body Washes E, G, T and U and in Control Body Washes A and L was evaluated. The body wash products comprising the capsules were stored during four weeks at 40° C. and the amount of perfume having leaked out of the capsules was measured by SPME and GC-MS analysis.

The results are summarized in the following table.

TABLE 24

Storage stability of the capsules of the invention in Body Washes E, G, T and U and in Control Body Washes A and L.

| Body Wash of the invention | Amount of perfume that leaked out of the capsules [%] | Amount of perfume that leaked out of the control capsules [%] | Corresponding Body Wash control |
|---|---|---|---|
| Body Wash E | 1 | 26 | Control A |
| Body Wash G | 1 |  |  |
| Body Wash T | 10 | 89 | Control L |
| Body Wash U | 6 |  |  |

It is apparent from these results that each of the capsules of the present invention was more stable in the body wash base than the corresponding control, in which only the aliphatic polyisocyanate was used, thus showing that combining an aromatic polyisocyanate with an aliphatic polyisocyanate in the claimed ratios improves the storage stability of polyurea microcapsules in a body wash base.

Example 29

Preparation of a Roll-On Antiperspirant Deodorant Product Comprising the Polyurea Microcapsules of the Invention A roll-on antiperspirant deodorant emulsion formulation was prepared by admixing the ingredients listed in Table 25, in the amounts indicated. The percentages are defined by weight relative to the total weight of the roll-on antiperspirant deodorant formulation.

TABLE 25

Composition of the roll-on antiperspirant deodorant formulation

| Ingredient | Amount [%] w/w |
|---|---|
| Brij 72[1] | 3.25 |
| Brij 721[2] | 0.75 |
| Arlamol E[3] | 4.00 |
| Locron L[4] | 40.00 |
| Water | 52.00 |

[1]Origin: Croda
[2]Origin: Croda
[3]Origin: Croda
[4]Origin: Clariant

Deodorants E, G, T and U were prepared by mixing Capsules E, G, T and U at 1.26% by weight, relative to the total weight of the roll-on antiperspirant deodorant into the roll-on antiperspirant deodorant emulsion formulation prepared above.

Example 30 (Comparative)

Preparation of a Roll-On Antiperspirant Deodorant Comprising the Polyurea Microcapsules of Examples 9 to 12

Control Deodorants A, H, L and M were prepared by adding Controls A, H, L and M at 1.26% by weight, relative to the total weight of the roll-on antiperspirant deodorant into the roll-on antiperspirant deodorant emulsion formulation prepared in Example 29.

Example 31

Olfactive Performance of the Polyurea Microcapsules of the Invention in Roll-On Antiperspirant Deodorant The olfactive performance of Capsules E and G as well as that of Controls A and H was evaluated in the corresponding deodorants of Examples 29 and 30.

An amount of 0.15 g of deodorant was spread on a paper blotter (4.5 cm*12 cm) and left to dry for 1 hour at room temperature before evaluating. The intensity of the perception of the perfume on the blotters treated with the deodorants was evaluated by a panel of 10 trained panelists. They were asked to rub gently the blotters with one finger and then to rate the intensity of the perfume perception on a scale ranging from 0 to 10, wherein 0 means no odour and 10 means very strong odour. The results are summarized in the following table.

TABLE 26

Olfactive performance of Capsules E and G, and of Controls A and H in roll-on antiperspirant deodorant

| Capsule of the invention | Olfactive performance of the capsules of the invention | Olfactive performance of the Control | Corresponding control |
| --- | --- | --- | --- |
| Capsules E | 8.3 | 7.60 | Control A |
|  |  | 8.00 | Control H |
| Capsules G | 8.2 | 7.60 | Control A |
|  |  | 8.00 | Control H |

It is clear from these results that after rubbing, the perfume intensity was slightly more intense on the blotters treated with the roll-on anti-perspirant deodorant containing the capsules of the invention, than on blotters treated with the roll-on anti-perspirant deodorant containing the control capsules. Therefore, the perfume is perceived more intensely when the capsules are made with a combination of an aromatic and an aliphatic polyisocyanate in the claimed ratios than when the capsules are made with an aromatic polyisocyanate alone or with an aliphatic polyisocyanate alone.

Example 32

Stability of the Polyurea Microcapsules of the Invention in a Roll-On Antiperspirant Deodorant The storage stability of the capsules in Deodorants E, G, T and U and in Control Deodorants A and L was evaluated. The deodorants were stored for 4 weeks at 45° C. and the amount of perfume having leaked out of the capsules was measured by SPME and GC-MS analysis. The results are summarized in the following table.

TABLE 27

Storage stability of the capsules of the invention in Deodorants E, G, T and U and in Control Deodorants A and L.

| Deodorant of the invention | Amount of perfume that leaked out of the capsules [%] | Amount of perfume that leaked out of the control capsules [%] | Corresponding Deodorant control |
| --- | --- | --- | --- |
| Deodorant E | 2 | 31 | Control A |
| Deodorant G | 1 |  |  |
| Deodorant T | 14 | 90 | Control L |
| Deodorant U | 9 |  |  |

It is apparent from these results that each of the capsules of the present invention was more stable in the roll-on anti-perspirant deodorant base than the corresponding control, in which only the aliphatic polyisocyanate was used, thus showing that combining an aromatic polyisocyanate with an aliphatic polyisocyanate in the claimed ratios improves the storage stability of polyurea microcapsules in a roll-on anti-perspirant deodorant base.

Example 33

Preparation of a Hair Shampoo Comprising the Polyurea Microcapsules of the Invention A hair shampoo formulation was prepared by admixing the ingredients listed in Table 28, in the amounts indicated. The percentages are defined by weight relative to the total weight of the hair shampoo formulation.

TABLE 28

Composition of the hair shampoo formulation

| Ingredient | Amount [%] w/w |
| --- | --- |
| Jaguar C-14S[1] | 0.4 |
| Dehyton AB-30[2] | 7.0 |
| Texapon NSO IS[3] | 45.0 |
| Dow Corning 2-1691 emulsion | 3.0 |
| Cutina AGS[4] | 0.9 |
| Rewomid IPP 240[5] | 1.2 |
| Cetyl alcohol | 1.2 |
| Glydant plus liquid[6] | 0.3 |
| Water | 41.0 |

[1]Origin: Rhodia
[2]Origin: Cognis
[3]Origin: Cognis
[4]Origin: Cognis
[5]Origin: Degussa
[6]Origin: Lonza Shampoos E, G, T and U were prepared by mixing Capsules E, G, T and U at 0.5% by weight, relative to the total weight of the shampoo into the hair shampoo formulation to prepared above.

Example 34 (Comparative)

Preparation of a Hair Shampoo Comprising the Polyurea Microcapsules of Examples 9 to 12

Control Shampoos A, H, L and M were prepared by adding Controls A, H, L and M at 0.5% by weight, relative to the total weight of the hair shampoo into the hair shampoo formulation prepared in Example 33.

Example 35

Olfactive Performance of the Polyurea Microcapsules of the Invention in Hair Shampoo The olfactive performance of Capsules E, G, T and U as well as that of Controls A, H, L and M was then evaluated in the corresponding hair shampoo of Examples 33 and 34.

A 10 g hair swatch was first washed with 2.5 g of the shampoo, rinsed for 30 seconds under tap water at 37° C. before repeating the same wash/rinse operation a second time. The hair swatch was then left to dry for 6 hours at room temperature before evaluating. The intensity of the perception of the perfume on the hair swatches washed with the shampoos was evaluated by a panel of 10 trained panelists. They were asked to comb gently the hair swatches 3 times and then to rate the intensity of the perfume perception on a scale ranging from 1 to 7, wherein 1 means no odour and 7 means very strong odour. The olfactive performance of Capsules T and U as well as that of Controls L and M was also evaluated using the same method after a drying time of 24 hours. The results are summarized in the following table.

TABLE 29

Olfactive performance of Capsules E, G, T and U and of Controls A, H, L and M in hair shampoo

| Capsule of the invention | Olfactive performance of the capsules of the invention | Olfactive performance of the Control | Corresponding control |
|---|---|---|---|
| Capsules E | 2.80 | 2.60 | Control A |
|  |  | 2.50 | Control H |
| Capsules G | 2.70 | 2.60 | Control A |
|  |  | 2.50 | Control H |
| Capsules T (6 hours) | 4.10 | 3.90 | Control L (6 hours) |
|  |  | 3.70 | Control M (6 hours) |
| Capsules U (6 hours) | 4.30 | 3.90 | Control L (6 hours) |
|  |  | 3.70 | Control M (6 hours) |
| Capsules T (24 hours) | 3.35 | 3.25 | Control L (24 hours) |
|  |  | 2.90 | Control M (24 hours) |
| Capsules U (24 hours) | 3.40 | 3.25 | Control L (24 hours) |
|  |  | 2.90 | Control M (24 hours) |

It is clear from these results that the perfume intensity was slightly more intense after combing on the hair swatches washed with the hair shampoo containing the capsules of the invention than on hair swatches washed with the hair shampoo containing the control capsules. Therefore, the perfume is perceived more intensely when the capsules are made with a combination of an aromatic and an aliphatic polyisocyanate in the claimed ratios than when the capsules are made with an aromatic polyisocyanate alone or with an aliphatic polyisocyanate alone.

Example 36

Stability of the Polyurea Microcapsules of the Invention in a Hair Shampoo

The storage stability of the capsules in Shampoos E, G, T and U and in Control Shampoos A and L was evaluated. The hair shampoos were stored for 2 weeks at 40° C. and the amount of perfume having leaked out of the capsules was measured by SPME and GC-MS analysis. The results are summarized in the following table.

TABLE 30

Storage stability of the capsules of the invention in Shampoos E, G, T and U and in Control Shampoos A and L.

| Shampoo of the invention | Amount of perfume that leaked out of the capsules [%] | Amount of perfume that leaked out of the control capsules [%] | Corresponding shampoo control |
|---|---|---|---|
| Shampoo E | 1 | 28 | Control A |
| Shampoo G | 1 |  |  |
| Shampoo T | 15 | 100 | Control L |
| Shampoo U | 10 |  |  |

It is apparent from these results that each of the capsules of the present invention was more stable in the hair shampoo base than the corresponding control, in which only the aliphatic polyisocyanate was used, thus showing that combining an aromatic polyisocyanate with an aliphatic polyisocyanate in the claimed ratios improves the storage stability of polyurea microcapsules in a hair shampoo base.

Example 37

Preparation of a Rinse-Off Hair Conditioner Comprising the Polyurea Microcapsules of the Invention Rinse-off hair conditioners (herein after Rinse-Off) E, G, T and U were prepared by mixing Capsules E, G, T and U at 0.5% by weight, relative to the total weight of the rinse-off hair conditioner into the commercially available Pantene® rinse-off hair conditioner formulation (trademark of Procter and Gamble, USA).

Example 38 (Comparative)

Preparation of a Rinse-Off Hair Conditioner Comprising the Polyurea Microcapsules of Examples 9 to 12

Control Rinse-off hair conditioners (herein after Rinse-Off) A, H, L and M were prepared by mixing Capsules A, H, L and M at 0.5% by weight, relative to the total weight of the rinse-off hair conditioner into the commercially available Pantene® rinse-off hair conditioner formulation (trademark of Procter and Gamble, USA).

Example 39

Olfactive Performance of the Polyurea Microcapsules of the Invention in Rinse-Off Hair Conditioner The olfactive performance of Capsules E, G, T and U as well as that of Controls A, H, L and M was then evaluated in the corresponding rinse-off hair conditioner of Examples 37 and 38.

Hair swatches (10 g) were first washed with 2.5 g of the hair shampoo formulation prepared in Example 33 (unperfumed and without capsules), rinsed for 30 seconds under tap water at 37° C. before spreading 1 g of rinse-off hair-conditioner.

The hair swatches were then rinsed for 30 seconds under tap water at 37° C. and left to dry for at room temperature before evaluating. Rinse-off E and G and Control Rinse-off A and H were left to dry for 24 hours, whereas Rinse-off T and U and Control Rinse-off L and M were left to dry for 6 hours before evaluation.

The intensity of the perception of the perfume on the hair swatches treated with the above rinse-off hair conditioners was evaluated by a panel of 10 trained panelists. They were asked to comb gently the hair swatches 3 times and then to rate the intensity of the perfume perception on a scale ranging from 1 to 7, wherein 1 means no odour and 7 means very strong odour. The results are summarized in the following table.

TABLE 31

Olfactive performance of Capsules E, G, T and U and of Controls A, H, L and M in rinse-off hair conditioner

| Capsule of the invention | Olfactive performance of the capsules of the invention | Olfactive performance of the Control | Corresponding control |
|---|---|---|---|
| Capsules E | 2.90 | 2.50 | Control A |
|  |  | 2.30 | Control H |
| Capsules G | 2.60 | 2.50 | Control A |
|  |  | 2.30 | Control H |
| Capsules T | 3.90 | 3.30 | Control L |
|  |  | 2.70 | Control M |
| Capsules U | 3.50 | 3.30 | Control L |
|  |  | 2.70 | Control M |

It is clear from these results that the perfume intensity was more intense after combing on the hair swatches treated with the rinse-off hair conditioner containing the capsules of the invention than on hair swatches treated with the rinse-off hair conditioner containing the control capsules. Therefore, the perfume is perceived more intensely when the capsules are made with a combination of an aromatic and an aliphatic polyisocyanate in the claimed ratios than when the capsules are made with an aromatic polyisocyanate alone or with an aliphatic polyisocyanate alone.

Example 40

Stability of the Polyurea Microcapsules of the Invention in a Rinse-Off Hair Conditioner The storage stability of the capsules in Rinse-Off E, G, T and U and in Control Rinse-Off A and L was evaluated. The rinse-off hair conditioners were stored for 2 weeks at 40° C. and the amount of perfume having leaked out of the capsules was measured by SPME and GC-MS analysis. The results are summarized in the following table.

TABLE 32

Storage stability of the capsules of the invention in Rinse-Off E, G, T and U and in Control Rinse-off A and L.

| Rinse-off of the invention | Amount of perfume that leaked out of the capsules [%] | Amount of perfume that leaked out of the control capsules [%] | Corresponding Rinse-off control |
|---|---|---|---|
| Rinse-Off E | 13 | 64 | Control A |
| Rinse-Off G | 10 |  |  |

TABLE 32-continued

Storage stability of the capsules of the invention in Rinse-Off E, G, T and U and in Control Rinse-off A and L.

| Rinse-off of the invention | Amount of perfume that leaked out of the capsules [%] | Amount of perfume that leaked out of the control capsules [%] | Corresponding Rinse-off control |
|---|---|---|---|
| Rinse-Off T | 66 | 88 | Control L |
| Rinse-Off U | 51 |  |  |

It is apparent from these results that each of the capsules of the present invention was more stable in the rinse-off hair conditioner base than the corresponding control, in which only the aliphatic polyisocyanate was used, thus showing that combining an aromatic polyisocyanate with an aliphatic polyisocyanate in the claimed ratios improves the storage stability of polyurea microcapsules in a rinse-off hair conditioner base.

Example 41

Preparation of a Leave-On Hair Conditioner Comprising the Polyurea Microcapsules of the Invention A leave-on hair conditioner formulation was prepared by admixing the ingredients listed in Table 33, in the amounts indicated. The percentages are defined by weight relative to the total weight of the leave-on hair conditioner formulation.

TABLE 33

Composition of the leave-on hair conditioner formulation

| Ingredient | Amount [%] w/w |
|---|---|
| Water | 95.5 |
| Mirasil ADM-E[1] | 1.5 |
| Salcare SC 91[2] | 1.0 |
| Aculyn 46[3] | 1.0 |
| Wacker-Belsil DMC 6038[4] | 0.5 |
| Phenonip[5] | 0.5 |

[1]Origin: Rhodia
[2]Origin: Ciba
[3]Origin: Rohm & Haas
[4]Origin: Wacker
[5]Origin: Clariant Leave-On Hair Conditioners (herein after Leave-On) E, G, T and U were prepared by mixing Capsules E, G, T and U at 0.26% by weight, relative to the total weight of the leave-on hair conditioner into the leave-on hair conditioner formulation prepared above.

Example 42 (Comparative)

Preparation of a Leave-On Hair Conditioner Comprising the Polyurea Microcapsules of Examples 9 to 12

Control Leave-On Hair Conditioners (herein after Control Leave-On) A, H, L and M were prepared by adding Controls A, H, L and M at 0.26% by weight, relative to the total weight of the leave-on hair conditioner into the leave-on hair conditioner formulation prepared in Example 42.

Example 43

Olfactive Performance of the Polyurea Microcapsules of the Invention in Leave-On Hair Conditioner The olfactive performance of Capsules E, G, T and U as well as that of Controls A, H, L and M was then evaluated in the corresponding Leave-On of Examples 41 and 42.

Hair swatches (10 g) were first washed with 2.5 g of the shampoo formulation prepared in Example 33 (unperfumed and without capsules), rinsed for 30 seconds under tap water at 37° C. before spreading 0.5 g of leave-on hair-conditioner. The hair swatches treated with Leave-On E and G and with Control Leave-On A and H were left to dry for 24 h at room temperature before evaluating. The hair swatches treated with Leave-On T and U and with Control Leave-On L and M were left to dry for 6 hours at room temperature before evaluating.

The intensity of the perception of the perfume on the hair swatches treated with the leave-on hair conditioners was evaluated by a panel of 10 trained panelists. They were asked to comb gently the hair swatches 3 times and then to rate the intensity of the perfume perception on a scale ranging from 1 to 7, wherein 1 means no odour and 7 means very strong odour. The results are summarized in the following table.

TABLE 34

Olfactive performance of Capsules E, G, T and U and of Controls A, H, L and M in leave-on hair conditioner

| Capsule of the invention | Olfactive performance of the capsules of the invention | Olfactive performance of the Control | Corresponding control |
|---|---|---|---|
| Capsules E | 5.30 | 4.30 | Control A |
|  |  | 4.90 | Control H |
| Capsules G | 5.10 | 4.30 | Control A |
|  |  | 4.90 | Control H |
| Capsules T | 5.15 | 3.80 | Control L |
|  |  | 5.00 | Control M |
| Capsules U | 5.40 | 3.80 | Control L |
|  |  | 5.00 | Control M |

It is clear from these results that the perfume intensity was more intense after combing on the hair swatches treated with the leave-on hair conditioner formulation containing the capsules of the invention than on hair swatches treated with the leave-on hair conditioner formulation containing the control capsules. Therefore, the perfume is perceived more intensely when the capsules are made with a combination of an aromatic and an aliphatic polyisocyanate in the claimed ratios than when the capsules are made with an aromatic polyisocyanate alone or with an aliphatic polyisocyanate alone.

Example 44

Stability of the Polyurea Microcapsules of the Invention in a Leave-On Hair Conditioner The storage stability of the capsules in Leave-On E, G, T and U and in Control Leave-On A and L was evaluated. The leave-on hair conditioners were stored for 2 weeks at 45° C. and the amount of perfume having leaked out of the capsules was measured by SPME and GC-MS analysis. The results are summarized in the following table.

TABLE 35

Storage stability of the capsules of the invention in Leave-On E, G, T and D and in Leave-On A and L.

| Leave-On of the invention | Amount of perfume that leaked out of the capsules [%] | Amount of perfume that leaked out of the control capsules [%] | Corresponding Leave-On control |
|---|---|---|---|
| Leave-On E | 18 | 73 | Control A |
| Leave-On G | 15 |  |  |
| Leave-On T | 74 | 74 | Control L |
| Leave-On U | 45 |  |  |

It is apparent from these results that each of the capsules of the present invention was more stable in the leave-on hair conditioner base than the corresponding control, in which only the aliphatic polyisocyanate was used, thus showing that combining an aromatic polyisocyanate with an aliphatic polyisocyanate in the claimed ratios improves the storage stability of polyurea microcapsules in a leave-on hair conditioner base.

Example 45

Preparation of a Body Lotion Comprising the Polyurea Microcapsules of the Invention Body Lotions E, G, T and U were prepared by dispersing Capsules E, G, T and U at 1.25% by weight, relative to the total weight of the body lotion into a commercially available body lotion formulation (Bath & Body Work, USA).

Example 46 (Comparative)

Preparation of a Body Lotion Comprising the Polyurea Microcapsules of Examples 9 to 12

Control Body Lotions A, H, L and M were prepared by dispersing Capsules A, H, L and M at 1.25% by weight, relative to the total weight of the body lotion into a commercially available body lotion formulation (origin: Bath & Body Work, USA).

Example 47

Olfactive Performance of the Polyurea Microcapsules of the Invention in Body Lotion The olfactive performance of Capsules E, G, T and U as well as that of Controls A, H, L and M was then evaluated in the corresponding body lotions of Examples 45 and 46.

An amount of 0.15 g of each body lotion was spread on a paper blotter (4.5 cm*12 cm) and left to dry for 1 hour at room temperature before evaluating.

The intensity of the perception of the perfume on the blotters treated with the above body-lotions was evaluated by a panel of 10 trained panelists. They were asked to rub gently the blotters with one finger and then to rate the intensity of the perfume perception on a scale ranging from 0 to 10, wherein 0 means no odour and 10 means very strong odour. The results are summarized in the following table.

TABLE 36

Olfactive performance of Capsules E, G, T and U and of Controls A, H, L and M in body lotion

| Capsule of the invention | Olfactive performance of the capsules of the invention | Olfactive performance of the Control | Corresponding control |
|---|---|---|---|
| Capsules E | 7.00 | 6.10 | Control A |
|  |  | 5.30 | Control H |
| Capsules G | 6.80 | 6.10 | Control A |
|  |  | 5.30 | Control H |
| Capsules T | 6.40 | 6.10 | Control L |
|  |  | 6.00 | Control M |
| Capsules U | 6.20 | 6.10 | Control L |
|  |  | 6.00 | Control M |

It is clear from these results that the perfume intensity was more intense after rubbing the blotters treated with the body-lotion containing the capsules of the invention than after rubbing the blotters treated with the body-lotion containing the control capsules. Therefore, the perfume is perceived more intensely when the capsules are made with a combination of an aromatic and an aliphatic polyisocyanate in the claimed ratios than when the capsules are made with an aromatic polyisocyanate alone or with an aliphatic polyisocyanate alone.

Example 48

Stability of the Polyurea Microcapsules of the Invention in a Body Lotion

The storage stability of the capsules in Body Lotions E, G, T and U and in Control Body Lotions A and L was evaluated. The body lotions were stored for 2 days at 25° C. and the amount of perfume having leaked out of the capsules was measured by SPME and GC-MS analysis. The results are summarized in the following table.

TABLE 37

Storage stability of the capsules of the invention in Body Lotions E, G, T and U and in Control Body Lotions A and L.

| Body Lotion of the invention | Amount of perfume that leaked out of the capsules [%] | Amount of perfume that leaked out of the control capsules [%] | Corresponding Body Lotion control |
|---|---|---|---|
| Body Lotion E | 5 | 59 | Control A |
| Body Lotion G | 3 |  |  |
| Body Lotion T | 16 | 85 | Control L |
| Body Lotion U | 9 |  |  |

It is apparent from these results that each of the capsules of the present invention was more stable in the body lotion base than the corresponding control, in which only the aliphatic polyisocyanate was used, thus showing that combining an aromatic polyisocyanate with an aliphatic polyisocyanate in the claimed ratios improves the storage stability of polyurea microcapsules in a body lotion base.

What is claimed is:

1. A process for the preparation of polyurea microcapsules for use in a consumer product, which process comprises:
  dissolving a first mixture of at least one aliphatic polyisocyanate and at least one aromatic polyisocyanate, both having at least two isocyanate functional groups, in a perfume to form a first solution with the aliphatic and aromatic polyisocyanates present in a molar ratio ranging from 80:20 to 10:90;
  adding to the first solution an aqueous solution that includes an emulsifier or a colloidal stabilizer to form a second mixture; and
  adding to the second mixture a polyamine to form with the polyisocyanate a slurry of microcapsules having a polyurea wall encapsulating the perfume therein in order to obtain microcapsules that exhibit less perfume leakage during storage in a consumer product that includes a surfactant and better odor performance during use of the consumer product that contains the microcapsules compared to a consumer product containing a surfactant and polyurea microcapsules made without the recited mixture of polyisocyanates.

2. The process according to claim 1, which further comprises forming a powder of polyurea microcapsules by drying the slurry of microcapsules.

3. The process according to claim 1, wherein the perfume is present in an amount of between 25 and 60% by weight relative to the total weight of the slurry of microcapsules.

4. The process according to claim 1, wherein the aromatic polyisocyanate comprises a phenyl, a toluyl, a xylyl, a naphthyl or a diphenyl moiety.

5. The process according to claim 1, wherein the aromatic polyisocyanate is selected from the group consisting of a polyisocyanurate of toluene diisocyanate, a trimethylol propane-adduct of toluene diisocyanate and a trimethylol propane-adduct of xylylene diisocyanate.

6. The process according to claim 1, wherein the aliphatic polyisocyanate is selected from the group consisting of a trimer of hexamethylene diisocyanate, a trimer of isophorone diisocyanate and a biuret of hexamethylene diisocyanate.

7. The process according to claim 1, wherein first mixture comprises a mixture of a biuret of hexamethylene diisocyanate with a trimethylol propane-adduct of xylylene diisocyanate.

8. The process according to claim 1, wherein the aliphatic polyisocyanate and the aromatic polyisocyanate are present in a molar ratio of 60:40 to 20:80.

9. The process according to claim 1, wherein the first mixture is present in an amount of between 2 and 20% by weight, relative to the total weight of the first solution.

10. The process according to claim 1, wherein the colloidal stabilizer is polyvinyl alcohol, a cellulose derivative, polyethylene oxide, a copolymer of polyethylene oxide and polyethylene or polypropylene oxide, a copolymer of acrylamide and acrylic acid, a cationic polymer or a mixture thereof.

11. The process according to claim 1, wherein the polyamine is selected from the group consisting of water soluble guanidine salts, guanidine, tris-(2-aminoethyl)amine, N,N,N',N'-tetrakis(3-aminopropyl)-1,4-butanediamine and N,N'-bis(3-aminopropyl)-ethylenediamine.

12. The process according to claim 1, wherein the aromatic polyisocyanate comprises a trimethylol propane-adduct of toluene diisocyanate and the aliphatic polyisocyanate comprises a biuret of hexamethylene diisocyanate.

13. Polyurea microcapsules obtained by the process according to claim 1 for use in a consumer product, which microcapsules exhibit less perfume leakage during storage in a consumer product that includes a surfactant and better odor performance during use of the consumer product that contains the microcapsules compared to a consumer product containing a surfactant and polyurea microcapsules made without the recited mixture of polyisocyanates.

14. A consumer product comprising a surfactant and microcapsules as defined in claim 13.

15. The consumer product according to claim 14 in the form of a shampoo, a hair conditioner, a soap, a body wash or another hygiene product, a cosmetic preparation, a body lotion, a deodorant or antiperspirant, a perfume, an aftershave lotion, a cologne, a solid or liquid detergent, an all-purpose cleaner, a fabric softener or refresher, an ironing water or a detergent, softener or drier sheet.

16. Polyurea microcapsules for use in a consumer product, the microcapsules comprising:
   a polyurea wall, which comprises the reaction product of the polymerisation between at least one polyisocyanate and at least one polyamine;
   a colloidal stabilizer or an emulsifier; and
   a perfume encapsuled within the polyurea wall;
   wherein the polyisocyanate is in the form of a mixture of at least one aliphatic polyisocyanate and at least one aromatic polyisocyanate in a respective molar ratio comprised between 80:20 to 10:90, both the aromatic and the aliphatic polyisocyanate comprising at least two functional isocyanate groups; and
   wherein the microcapsules exhibit less perfume leakage during storage in a consumer product that includes a surfactant and better odor performance during use of the microcapsules that contain the microcapsules compared to a consumer product containing a surfactant and polyurea microcapsules made without the recited mixture of polyisocyanates.

17. A consumer product comprising microcapsules as defined in claim 16.

18. The consumer product according to claim 17 in the form of a shampoo, a hair conditioner, a soap, a body wash or another hygiene product, a cosmetic preparation, a body lotion, a deodorant or antiperspirant, a perfume, an aftershave lotion, a cologne, a solid or liquid detergent, an all-purpose cleaner, a fabric softener or refresher, an ironing water or a detergent, softener or drier sheet.

19. The microcapsules according to claim 16, wherein the aromatic polyisocyanate comprises a trimethylol propane-adduct of toluene diisocyanate and the aliphatic polyisocyanate comprises a biuret of hexamethylene diisocyanate.

20. The consumer product according to claim 17, wherein, in the microcapsules, the aromatic polyisocyanate comprises a trimethylol propane-adduct of toluene diisocyanate and the aliphatic polyisocyanate comprises a biuret of hexamethylene diisocyanate.

* * * * *

UNITED STATES PATENT AND TRADEMARK OFFICE
CERTIFICATE OF CORRECTION

Page 1 of 1

PATENT NO. : 9,271,905 B2
APPLICATION NO. : 13/700526
DATED : March 1, 2016
INVENTOR(S) : Struillou et al.

It is certified that error appears in the above-identified patent and that said Letters Patent is hereby corrected as shown below:

In The Claims

Column 34:
Line 2 (claim 16, line 17), change "contain" to -- contains --.

Signed and Sealed this
Tenth Day of May, 2016

Michelle K. Lee
*Director of the United States Patent and Trademark Office*